United States Patent
Milz et al.

(10) Patent No.: US 10,517,653 B2
(45) Date of Patent: Dec. 31, 2019

(54) SURGICAL INSTRUMENTS AND METHODS

(71) Applicant: Stryker European Holdings I, LLC, Kalamazoo, MI (US)

(72) Inventors: Bryan D. Milz, Florida, NY (US); Frank Pinal, Jersey City, NJ (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 51 days.

(21) Appl. No.: 15/969,110

(22) Filed: May 2, 2018

(65) Prior Publication Data

US 2018/0317975 A1 Nov. 8, 2018

Related U.S. Application Data

(62) Division of application No. 15/084,020, filed on Mar. 29, 2016, now Pat. No. 9,987,053.

(51) Int. Cl.
*A61B 17/70* (2006.01)

(52) U.S. Cl.
CPC ...... *A61B 17/7068* (2013.01); *A61B 17/7076* (2013.01)

(58) Field of Classification Search
CPC combination set(s) only.
See application file for complete search history.

(56) References Cited

U.S. PATENT DOCUMENTS

| | | | |
|---|---|---|---|
| 7,892,239 B2 | 2/2011 | Warnick et al. | |
| 8,308,728 B2 | 11/2012 | Iott et al. | |
| 8,696,681 B2 | 4/2014 | Harris et al. | |
| 8,870,880 B2 | 10/2014 | Himmelberger et al. | |
| 8,986,389 B2 | 3/2015 | Lim et al. | |
| 9,271,842 B2 | 3/2016 | Davenport et al. | |
| 9,271,846 B2 | 3/2016 | Lim et al. | |
| 9,392,673 B2 | 7/2016 | Harris et al. | |
| 9,642,722 B2 | 5/2017 | Baynham | |
| 9,750,546 B2 * | 9/2017 | Semingson | A61B 17/708 |
| 2003/0208203 A1 | 11/2003 | Lim et al. | |
| 2008/0065082 A1 | 3/2008 | Chang et al. | |
| 2008/0091211 A1 | 4/2008 | Gately | |
| 2008/0221694 A1 | 9/2008 | Warnick et al. | |
| 2008/0306489 A1 | 12/2008 | Altarac et al. | |
| 2010/0256759 A1 | 10/2010 | Hansell et al. | |
| 2010/0256760 A1 | 10/2010 | Hansell | |
| 2010/0256764 A1 | 10/2010 | Tsuang et al. | |
| 2012/0265305 A1 * | 10/2012 | Oh | A61F 2/4611 623/17.16 |
| 2013/0060337 A1 * | 3/2013 | Petersheim | A61F 2/447 623/17.16 |
| 2013/0144339 A1 * | 6/2013 | Choi | A61B 17/7047 606/249 |
| 2014/0018815 A1 | 1/2014 | Kirschman | |
| 2014/0142642 A1 | 5/2014 | Wallenstein et al. | |
| 2017/0071753 A1 * | 3/2017 | Josse | A61F 2/4611 |

* cited by examiner

*Primary Examiner* — Lynnsy M Summitt
(74) *Attorney, Agent, or Firm* — Lerner, David, Littenberg, Krumholz & Mentlik, LLP (57) ABSTRACT

Various surgical instruments, implants, and their methods of use are disclosed. The surgical instruments are usable to insert various implants into a patient through an access portal in a minimally-invasive manner. The implants are rotatable between different orientations using the instruments to change the footprint of the implant and allow the implant to be inserted through the minimally-invasive access portal.

6 Claims, 9 Drawing Sheets

SURGICAL INSTRUMENTS AND METHODS

CROSS-REFERENCE TO RELATED APPLICATIONS

This application is a divisional of U.S. application Ser. No. 15/084,020, filed on Mar. 29, 2016, the disclosure of which is hereby incorporated herein by reference.

BACKGROUND OF THE INVENTION

Spinal stenosis often involves narrowing of the spinal canal and pinching of the spinal cord and nerves, causing pain in the back and legs. Typically, with age, a person's ligaments may thicken, intervertebral discs may deteriorate, and facet joints may break down contributing to spinal stenosis. Injury, heredity, arthritis, changes in blood flow, and other causes may also contribute to spinal stenosis. Treatments for such conditions vary, though such treatments typically involve open surgery to repair tissue and/or allow for implantation of an implant.

A recent advancement, minimally invasive surgery, is becoming increasingly important—patient trauma and recovery time is vastly reduced, amongst other benefits. In general, such surgeries involve making a small incision in the skin and tissue of a patient, inserting a minimally-invasive access portal (e.g., a cannula or retractor) in the incision, and subsequently performing surgery through the access portal in a less-intrusive manner. In spinal surgery, as an example, an implant or other device is moved through the access portal and engaged with part of the patient's spine (e.g., to assist with fusion, stabilization, etc.). Yet, it is often difficult to manipulate the implant or other device through the access portal. It is also desirable to use an access portal with the smallest exposure (e.g., diameter) possible so that the surgery exacts the least trauma on the patient. Current instruments and implants are cumbersome in this regard, and make it difficult to use smaller-footprint access portals.

Therefore, there exists a need for improved surgical instruments, implants, and methods to overcome the foregoing deficiencies.

BRIEF SUMMARY OF THE INVENTION

A first aspect of the invention provides a surgical system comprising an implant and a first instrument. The first instrument comprises a hollow body and an actuation member movably engaged to a locking mechanism, wherein movement of the actuation member from a first position to a second position causes the locking mechanism to move from an unlocked state to a locked state. The first instrument further includes a connection mechanism engageable with the implant, wherein, after engagement of the connection mechanism with the implant, movement of the locking mechanism from its unlocked state to its locked state locks the connection mechanism to the implant, and movement of the locking mechanism from its locked state to its unlocked state unlocks the connection mechanism from the implant, the implant being rotatable while engaged to the connection mechanism from a first orientation in which the implant has a first footprint in a horizontal direction to a second orientation in which the implant has a second footprint in the horizontal direction smaller than the first footprint. The first instrument also has an activation sleeve engaged to a pivoting member, the pivoting member having a surface shaped to contact the implant and retain the implant in its second orientation.

In embodiments of this first aspect, the pivoting member is engaged to the activation sleeve via a spring that biases the pivoting member into a first orientation transverse to the activation sleeve. Further, the system may include a drive shaft operatively engaged to the actuation member and to the locking mechanism, the actuation member comprising a knob rotatably engaged to the instrument, wherein rotation of the knob relative to the instrument causes longitudinal movement of the drive shaft, thereby resulting in movement of the locking mechanism from its unlocked state to its locked state.

A second aspect of the invention includes a method of performing surgery comprising (i) engaging a first surgical instrument with an implant, (ii) moving a pivoting member of the first surgical instrument from a first distal position to a second relatively more proximal position, (iii) rotating the pivoting member from a first orientation in which the pivoting member occupies a first footprint in a horizontal direction to a second orientation in which the pivoting member occupies a second footprint in the horizontal direction smaller than the first footprint, (iv) rotating the implant from a first orientation in which the implant occupies a first footprint in the horizontal direction to a second orientation in which the implant occupies a second footprint in the horizontal direction smaller than the first footprint, (v) subsequently biasing a surface of the pivoting member against the implant so that the pivoting member and the implant are secured in their second orientations, (vi) inserting the instrument with the implant attached in its second orientation through an access portal extending through skin and tissue of a patient, (vii) after the implant passes through the access portal, rotating the pivoting member from its second orientation back to its first orientation, (viii) engaging the pivoting member with the implant so that the implant is rotated from its second orientation back to its first orientation, and (ix) engaging the implant to anatomy in the patient. Although some steps may be numbered in the disclosure, no ordering is implied by the numbering and certain steps of the method may be performed in a different order than set forth by the numbering.

In embodiments of the second aspect, the method further comprises (i) inserting a second surgical instrument through the first surgical instrument, (ii) engaging the second surgical instrument with the implant, and (iii) moving the second surgical instrument while engaged to the implant so that the implant either expands or contracts.

A third aspect of the invention includes a surgical system comprising an implant and a first instrument. The first instrument includes a body and an actuation member movably engaged to a locking mechanism, wherein movement of the actuation member from a first position to a second position causes the locking mechanism to move from an unlocked state to a locked state. The instrument also has a connection mechanism engageable with the implant, wherein, after engagement of the connection mechanism with the implant, movement of the locking mechanism from its unlocked state to its locked state locks the connection mechanism to the implant, and movement of the locking mechanism from its locked state to its unlocked state unlocks the connection mechanism from the implant, the implant being rotatable while engaged to the connection mechanism from a first orientation in which the implant has a first footprint in a horizontal direction to a second orientation in which the implant has a second footprint in the horizontal direction smaller than the first footprint. The first instrument further comprises an activation sleeve engaged to a pivoting member, the pivoting member being rotatable relative to the activation sleeve from a first orientation in which the pivoting member has a first footprint in the horizontal direction to a second orientation in which the pivoting member has a second footprint in the horizontal direction smaller than the first footprint, wherein the pivoting member has a surface shaped to contact the implant and retain the implant in its second orientation when the pivoting member is in its second orientation.

In certain embodiments, the pivoting member is movable in a longitudinal direction from a first distal position to a second more proximal position and, when the pivoting member is in the first distal position with the surface of the pivoting member engaged to the implant, the pivoting member and the implant are fixedly secured their second orientations.

In a fourth aspect of the invention, a surgical instrument for use in minimally invasive surgery is provided, the surgical instrument comprising a rotational member, a first sliding member, a second sliding member, a compressible member, and a pivoting member, wherein an uninterrupted cannulation extends through each of the rotational member, first sliding member, second sliding member, compressible member and pivoting member, the cannulation adapted to allow passage of a second instrument therethrough. Embodiments of this fourth aspect may encompass wherein the pivoting member includes an end adapted to engage with an implant and rotate the implant from a first position to a second position. In the first position, the implant may have a first footprint and, in the second position, the implant may have a second footprint that is smaller than the first footprint. In other embodiments, the second instrument is engageable with an implant to expand or contract the implant.

The instruments and methods provided herein are useful for inserting implants, in a minimally-invasive manner, through a relatively small access portal in a first orientation where the implant has a first footprint, and then moving the implant into a second orientation once the implant passes through the access portal so that the implant has a second footprint larger than the first footprint. Thus, the trauma and time frame of a surgical procedure can be improved.

BRIEF DESCRIPTION OF THE DRAWINGS

A more complete appreciation of the subject matter of the present invention and of the various advantages thereof can be realized by reference to the following detailed description in which reference is made to the accompanying drawings in which:

FIGS. 6A-C are side, top, and bottom views of the instrument of FIG. 1 in use with an alternate implant.

DETAILED DESCRIPTION

In describing certain aspects of the present invention, specific terminology will be used for the sake of clarity. However, the invention is not intended to be limited to any specific terms used herein, and it is to be understood that each specific term includes all technical equivalents, which operate in a similar manner to accomplish a similar purpose.

Figure 2A:
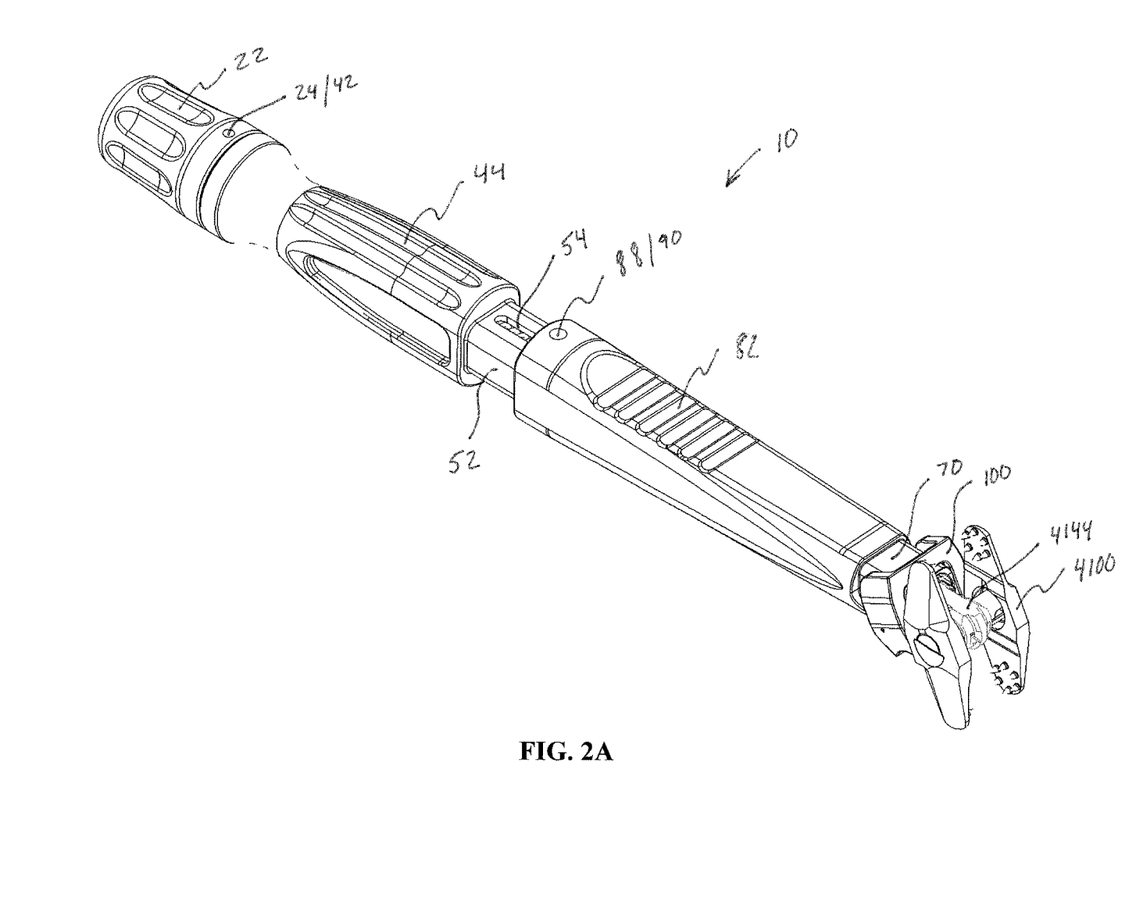
FIGS. 2A-C are perspective, top, and cross-sectional views of the instrument of FIG. 1 attached to an implant, with the instrument and implant in a first orientation.
Figure 2B:
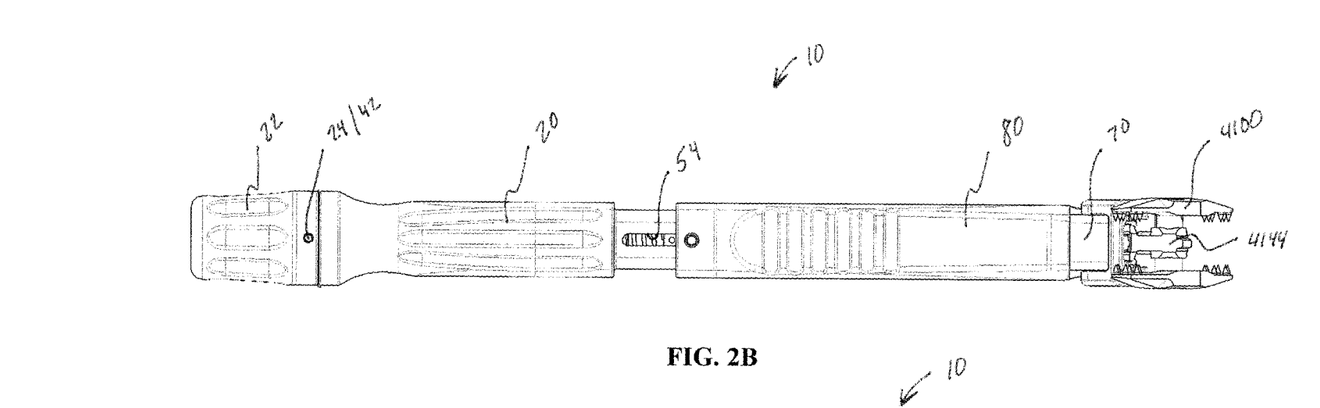
Figure 2C:
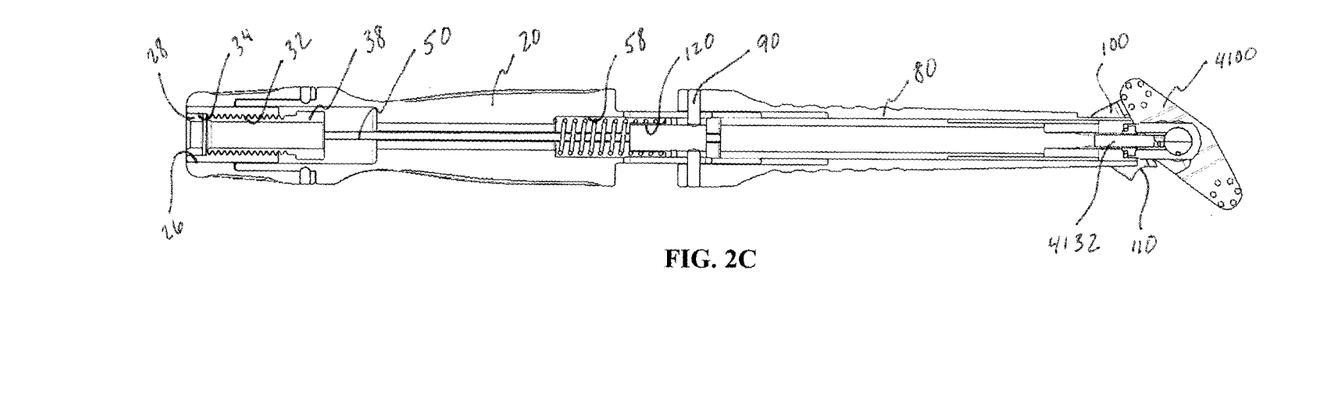

FIGS. 2A-C depict a surgical instrument 10, according to an embodiment of the invention. As described in more detail below, instrument 10 may be used to pivot an implant 4100 (FIGS. 5A-B) into different orientations (e.g., a "vertical" orientation, and a "horizontal" orientation) for insertion through an access portal, such as a cannula, retractor, etc. (not shown). Pivoting implant 4100 in this manner using instrument 10 allows for easy insertion through a relatively small access portal, resulting in less trauma to the patient, reduced surgery time, and reduced recovery time. Instrument 10 is therefore effective at implanting various implants (e.g., implant 4100) through an access portal in a minimally-invasive manner.

Although a variety of implants are usable with the instruments disclosed herein, Applicant has developed a number of implants that are particularly suitable for use with instrument 10. As an example, various implants are disclosed in Applicant's co-pending application U.S. Patent Pub. No. 2013/0144339 ("the '339 Publication"), filed as U.S. application Ser. No. 13/679,986, which is hereby incorporated by reference herein. It is understood that any of the implants disclosed in the '339 Publication are usable with the instruments described herein, although a particular embodiment of an implant from the '339 Publication is referred to throughout the present application as an example. The particular implant of the '339 Publication referenced herein is implant 4100 of FIGS. 40A-42B. FIGS. 40A-B of the '339 Publication have been reproduced herein as FIGS. 5A-B, with the same reference numerals being used, for ease of reference.

Figure 5A:
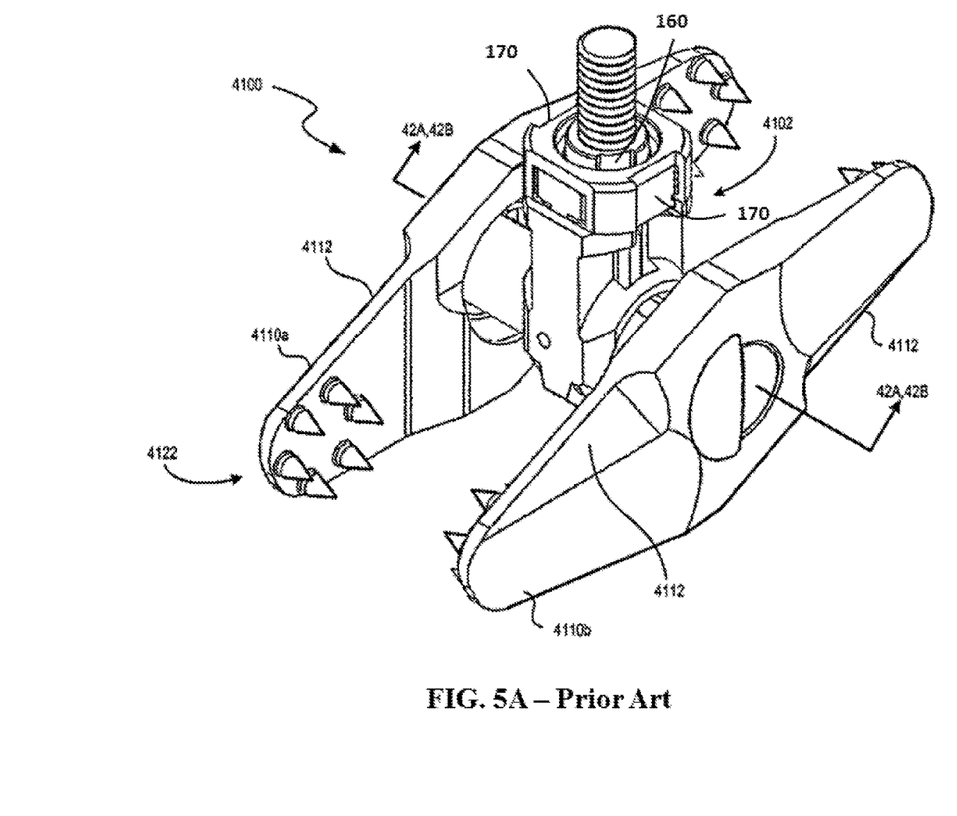
FIGS. 5A-B are perspective and exploded views of an embodiment of an implant that is usable with the surgical instruments of FIG. 1-4B.
Figure 5B:
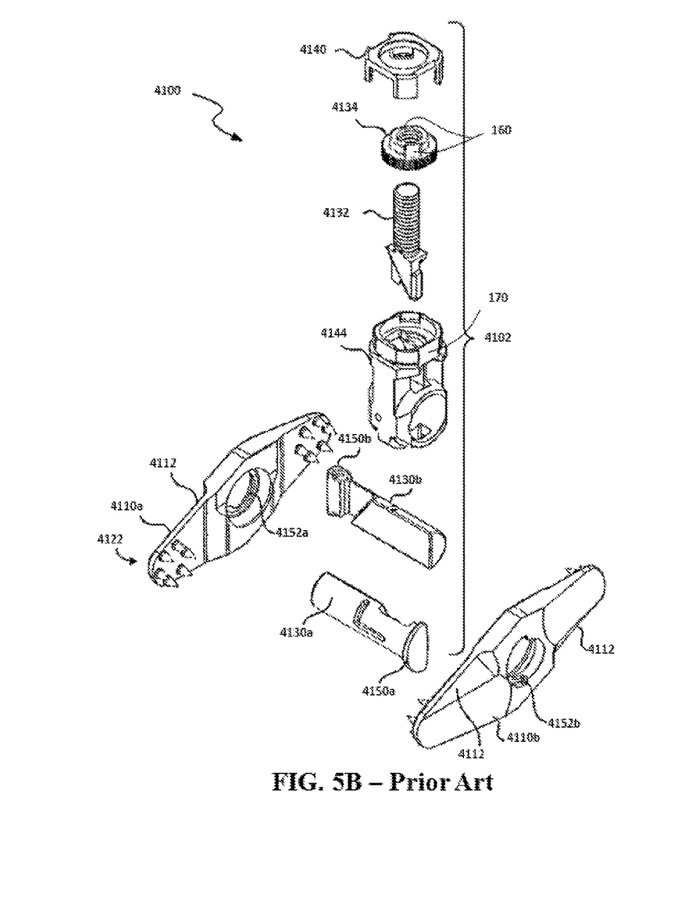

Continuing with the exemplary implant, as reproduced in FIGS. 5A-B, implant 4100 includes a clamp assembly 4122 comprising wings 4110 (identified individually as wings 4110a, 4110b), and an actuator assembly 4102 for actuating wings 4110. Implant 4100 can be implanted, for example, between the spinous processes of adjacent vertebrae of a patient, in the manner described in the '339 Publication (e.g., with the implant 4110's wings clamped to the processes). Actuator assembly 4102 includes an actuator 4132 having a threaded shaft, an actuator adjuster 4134, a cover 4140, a body 4144, and guides 4130a, 4130b. Guides 4130a, 4130b are attached to wings 4110 (e.g., via receiving features 4152a, 4152b), and rotation of actuator adjuster 4134 in a first direction causes actuator 4132 to move outward away from guides 4130a, 4130b within body 4144, allowing wings 4110 to be at their maximum separation, while rotation of actuator adjuster 4134 in a second direction causes actuator 4132 to move inwards towards guides 4130a, 4130b within body 4144, resulting in wings 4110 moving towards each other to a compressed state. FIG. 42A of the '339 Publication illustrates wings 4110 in a separated state, while FIG. 42B illustrates wings 4110 in a compressed state (e.g., for attachment to a patient's spinous processes). The particular means by which wings 4410 are moved toward and away from each other is described in more detail in the '339 Publication.

Actuator adjuster 4134 also includes one or more female mating features 160 for engaging with a tool 140 (described below). Tool 140 is used to rotate actuator adjuster 4134 and cause expansion or contraction of wings 4110 of implant 4100, as detailed above. Additionally, body 4144 includes female mating features 170 for engaging with a part of instrument 10, as described in more detail below.

Figure 1:
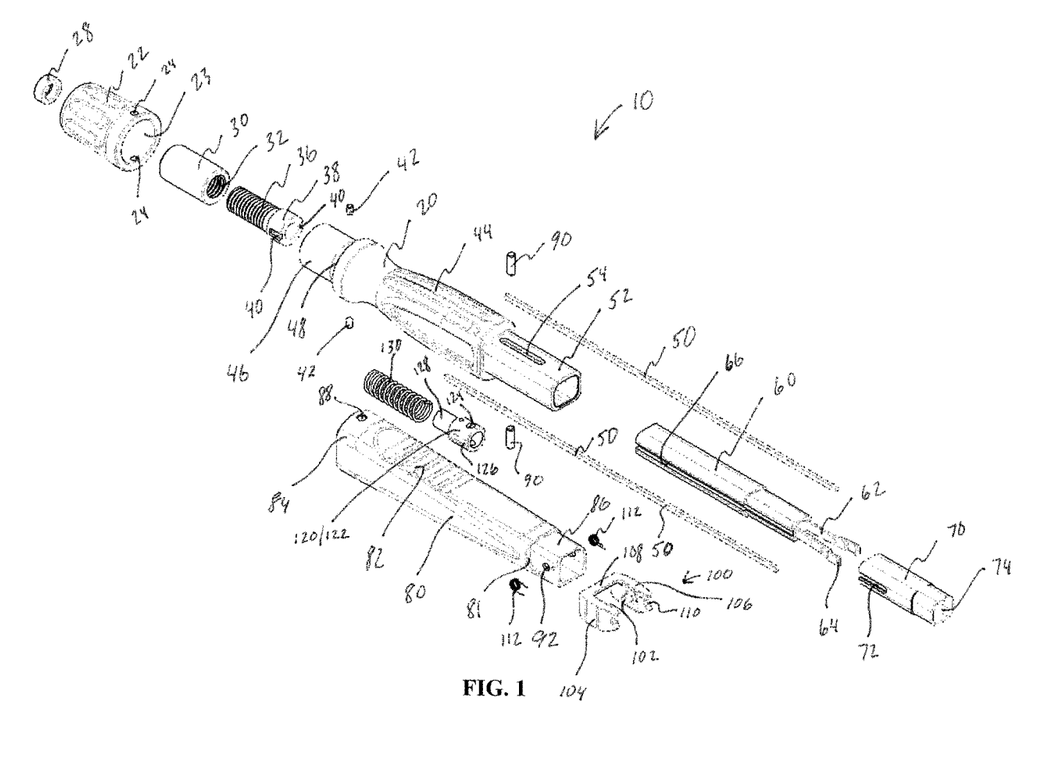
FIG. 1 is an exploded view of a surgical instrument according to an embodiment of the invention.

Referring now to FIG. 1, in an embodiment, instrument 10 is engageable with an implant, for example implant 4100, and usable to insert implant 4100 through a minimally-invasive access portal. In this regard, instrument 10 includes a spring clip 60 for attaching to implant 4110 (or any other implant, including any of those of the '339 Publication, as described above). Spring clip 60 has spring arms 62 that are biased outwards and are engageable with implant 4110 via female mating features 170 on body 4144. In particular, arms 62 have hooks 64 that grasp female mating features 170 of body 4144 to engage instrument 10 to implant 4100.

Continuing with this embodiment, a sleeve 70 is positionable over spring clip 60 and is movable relative thereto for releasably locking arms 62 to female mating features 170, and thus implant 4100. As an example, sleeve 70 includes an opening 74 through which arms 62 may extend. Sleeve 70 is moveable from a first position in which arms 62 extend out of opening 74 and are not covered or are only partly covered by sleeve 70, thereby allowing arms 62 to assume their biased orientation (e.g., spaced apart), to a second position in which sleeve 70 covers part or all of arms 62 causing arms 62 to move toward each other. In use, arms 62 are engageable with female mating features 170 of implant while sleeve 70 is in its first position. Alternatively, in the first position, arms 62 can be positioned adjacent female mating features 170. Sleeve 70 is then movable to its second position to cause arms 62 to move towards each other, or at least prevent arms 62 from moving away from each other. In the second position, hooks 64 securely engage female mating features 170, and arms 62 are locked in position in engagement with female mating features 170. In other words, in the second position, sleeve 70 prevents arms 62 and hooks 64 from disengaging with female mating features 170 since sleeve 70 covers arms 62 and arms 62 are unable to move outwards away from each other.

Movement of sleeve 70 from its first position to its second position is achieved by a user interface, such as a rotatable knob 22 of instrument 10. Indeed, in an embodiment, a set of drive rails 50 are attached (e.g., welded) to slots 72 on sleeve 70 and rotation of knob 22 causes movement of drive rails 50 and sleeve 70. As an example, drive rails 50 extend from sleeve 70 and are connected to a threaded drive insert 36 positioned in a cavity 23 of knob 22. An unthreaded part 38 of drive insert 36 includes a set of cutouts or recesses 40, and drive rails 50 are securely attached to drive insert 36 within such recesses 40 (e.g., by welding). A threaded knob insert 30 is also provided within cavity 23 of knob 22, which is configured to receive the threaded part of drive insert 36. In an embodiment, cavity 23 extends to a proximal bore 26 within knob 22, and knob insert 30 is securely affixed (e.g., welded or adhered) within internal cavity 23 and proximal bore 26, as shown in the cross-section of FIG. 2C. In this manner, rotation of knob 22 causes rotation of knob insert 30 which, due to its association with drive insert 36, causes movement of drive insert 36 in opposing directions.

Continuing with the embodiment shown in FIG. 1, a handle 20 with a gripping part 44 is also provided with instrument 10. First and second projections 46, 52 extend from gripping part 44, and a hollow bore extends through handle 20 (and necessarily projections 46, 52 and gripping part 44). The dimension of the hollow bore is such that first projection 46 can receive drive insert 36 and knob insert 30 therein, while second projection 52 receives drive rails 50 therein. Drive rails 50 and drive insert 36 are also movable relative to handle 20 within its hollow bore upon rotation of knob 22, as noted above. In particular, knob 22 includes openings 24 that receive pins 42. Handle 20 also has a circumferential groove 48 that extends around part or all of first projection 46 for receiving pins 42. As such, pins 42 can be placed in openings 24 so that pins 42 ride in circumferential groove 48 and allow knob 22 to rotate about handle 20 without relative axial movement. In other words, knob 22 can rotate relative to handle 20 without sliding longitudinally relative to handle 20. In this way, to cause movement of sleeve 70 from its first position to its second position, or vice versa, a user may simply rotate knob 22 relative to handle 20, causing threaded knob insert 30 to rotate and force drive insert 36 in a proximal or distal direction within handle 20. Since drive rails 50 are attached to drive insert 36 and sleeve 70, such movement causes sleeve 70 to move from its first position to its second position, or vice versa. In an embodiment, rotation of knob 22 in a clockwise direction causes distal movement of drive insert 36 (and consequently drive rails 50 and sleeve 70), while rotation of knob 22 in a counterclockwise direction causes proximal movement of drive insert 36 (and consequently drive rails 50 and sleeve 70). Thus, a user is afforded a simplified mechanism for moving sleeve 70 from its first position to its second position so as to lock or unlock arms 62 of spring clip 60. Instrument 10 can therefore easily be engaged or disengaged from implant 4100 in a secure manner.

Spring clip 60 may additionally include slots 66 for accommodating and/or guiding drive rails 50 during rotation of knob 22. In an embodiment, drive rails 50 are not securely attached to slots 66 and, instead, drive rails 50 slide along slots 66. Drive rails are therefore movable relative to and are in part guided by slots 66 of spring clip 60 during rotation of knob 22.

Continuing with the embodiment of FIG. 1, instrument 10 further includes a mechanism for rotating implant 4100 between vertical and horizontal orientations. A "horizontal" orientation can be one in which implant 4100 is transverse to a longitudinal axis of instrument 10, for example by about anywhere between about five to about ninety degrees (5-90°). A "vertical" orientation may be one in which implant 4100 is more or less in line with or parallel to the longitudinal axis, for example anywhere between about zero to about fifteen degrees (0-15°). In the horizontal orientation, implant 4100 has a footprint that is larger than a footprint of implant 4100 in the vertical orientation. Such rotation facilitates movement of implant 4100 through a small access portal—while implant 4100 is in the vertical orientation—as well as implantation of implant 4100 in an appropriate horizontal orientation between a patient's spinous processes after passage through the access portal.

One example of a swivel tip 100 is shown in FIGS. 2A-3C. Swivel tip 100 is capable of placing implant 4100 in its first "vertical" (FIGS. 3A-C) and second "horizontal" orientations (FIGS. 2A-C). As shown in FIG. 1, swivel tip 100 includes first and second arms 104, 106, each having a recess 110 and a bar 108 connecting arms 104, 106. Swivel tip 100 also has a set of projections 102 arranged on an inside part of each arm 104, 106 for attaching swivel tip 100 to an activation sleeve 80.

In one embodiment, activation sleeve 80 is a hollow sleeve designed to fit over second projection 52 of handle 20 at a first end 84, and receive spring clip 60 and sleeve 70 at a second end 86. Activation sleeve 80 also includes a gripping part 82 and openings 88 and, once first end 84 is positioned over second projection 52 of handle 20, pins 90 are insertable into openings 88 so as to ride within a set of channels 54 of handle 20. Activation sleeve 80 can therefore reciprocate relative to handle 20 in a controlled manner by an amount equal to the length of channels 54.

Activation sleeve 80 is also associated with an activation sleeve collar 120, which has a main body 122 with openings 124, a projection 128 extending from main body 122, and side channels 126 disposed on main body 122. Pins 90 are insertable into openings 88 of activation sleeve 80, through channels 54 of handle 20, and subsequently into openings 124 of activation sleeve collar 120. Additionally, a spring 130 may be positioned in a pocket 58 of handle 20 (FIGS. 2C and 3C) and also over projection 128 of activation sleeve collar 120 to control movement of activation sleeve 80. In particular, spring 130 is arranged in pocket 58 to contact an end/step thereof and also a step formed between main body 122 and projection 128 of activation sleeve collar 120. With pins 90 inserted into openings 88, through channels 54, and subsequently into openings 124 of activation sleeve collar 120, spring 130 is then able to bias activation sleeve 80 in a distal direction. In other words, activation sleeve 80 is predisposed to be in a distal position corresponding to the maximum length of spring 130 as spring 130 acts on activation sleeve collar 120. Due to activation sleeve collar 120's attachment to activation sleeve 80 via pins 90, spring 130 forces activation sleeve 80 distally.

To move activation sleeve 80 proximally, a user may opt to grasp gripping part 82 of activation sleeve 80 and pull it in a proximal direction against the force of spring 130. This causes the step of activation sleeve collar 120 to act on and compress spring 130, moving collar 120 and thus activation sleeve 80 attached thereto in a proximal direction. Through the action of spring 130, and the connection between activation sleeve 80 and activation sleeve collar 120 via pins 90, a user is therefore able to easily move activation sleeve 80 proximally by pulling on gripping part 82, and also move activation sleeve 80 distally by simply releasing gripping part 82. Such movement of activation sleeve 80 facilitates or causes corresponding movement of swivel tip 100, as described below.

Further to this embodiment, second end 86 of activation sleeve 80, as shown in FIG. 1, includes a set of openings 92 for receiving projections 102 of swivel tip 100. Additionally, a set of torsion springs 112 are positionable over projections 102 of swivel tip 100 and, when swivel tip 100 is engaged to activation sleeve 80 through openings 92, torsion springs 112 act to bias swivel tip 100 to a horizontal orientation, as shown in FIGS. 2A-C. Swivel tip 100 can be moved to a vertical orientation to coincide with the vertical orientation of implant 4100 by pulling on activation sleeve 80 via its gripping part 82 to move activation sleeve 80 and collar 120 proximally against spring 130. Here again, a "horizontal" orientation may be one in which swivel tip 100 is transverse to the longitudinal axis of instrument 10, for example, within a range of anywhere between about five to about ninety degrees (5-90°). A "vertical" orientation may be one in which swivel tip 100 is more or less in line with the longitudinal axis of instrument 10, for example anywhere between about zero to about fifteen degrees (0-15°).

In an embodiment, swivel tip 100 needs to be manually placed in the vertical orientation after retraction of activation sleeve 80 due to the constant biasing of torsion springs 112. In other words, once activation sleeve 80 is pulled proximally a sufficient distance, the user must manually rotate swivel tip 100 to its vertical orientation. In an embodiment, activation sleeve 80 may include a lock or other mechanism (not shown) for retaining sleeve 80 in its proximal position. The lock (not shown) may be released using a release mechanism (not shown) after moving swivel tip 100 to its vertical orientation. The interaction of swivel tip 100 with an implant, such as implant 4100, will be discussed below.

Figure 3A:
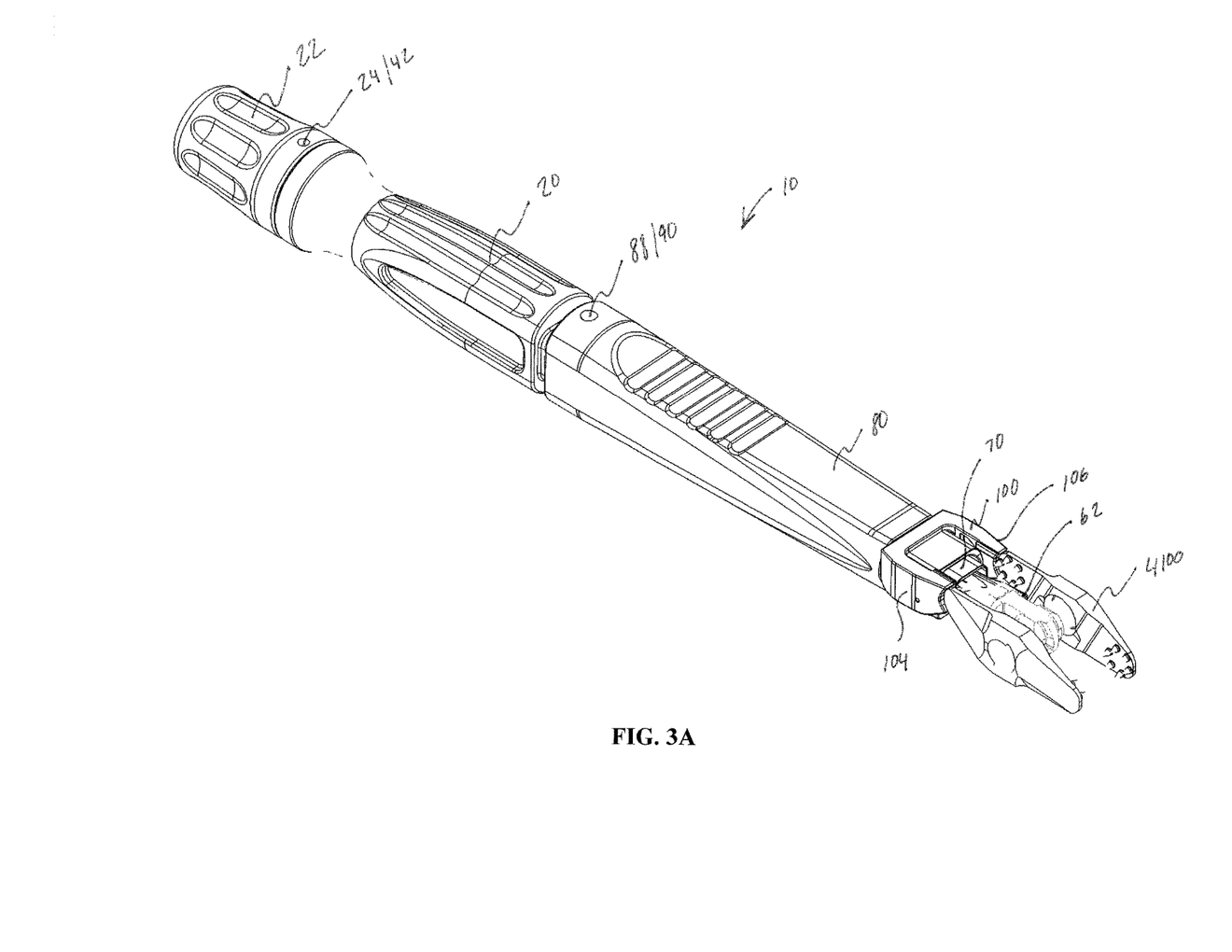
FIGS. 3A-C are perspective, top, and cross-sectional views of the instrument of FIG. 1 attached to an implant, with the instrument and implant in a second orientation.
Figure 3B:
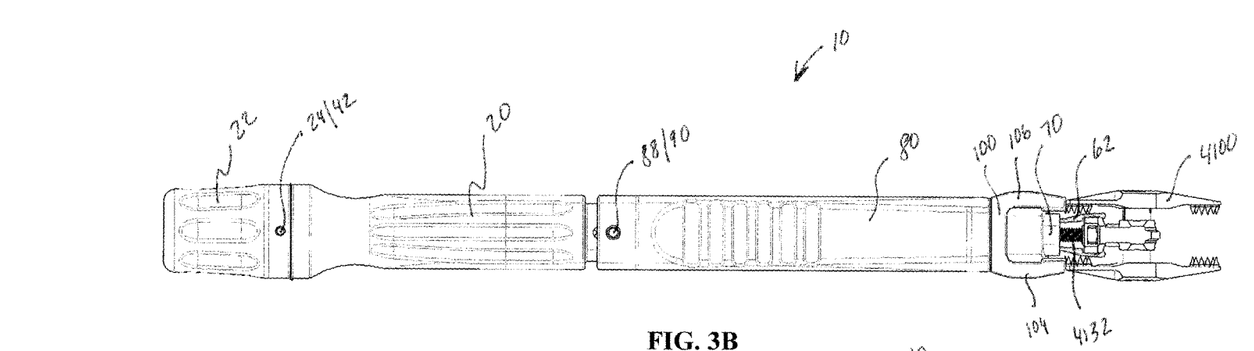
Figure 3C:
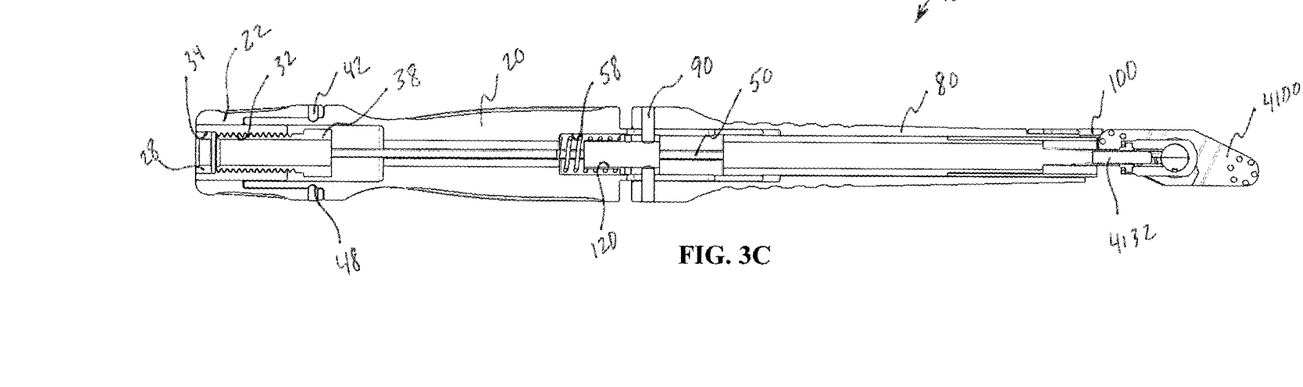
Figure 4A:
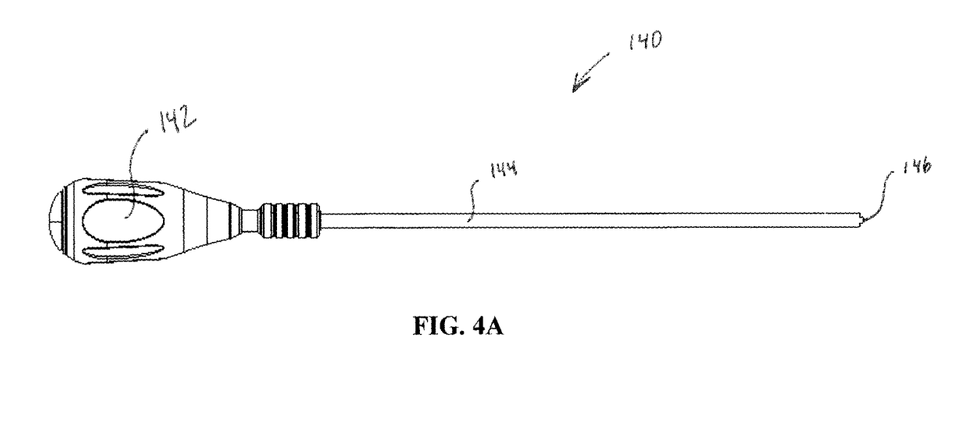
FIGS. 4A-B are perspective and cross-sectional views of the surgical instrument of FIG. 1 in use with a second surgical instrument for actuating the implant.
Figure 4B:
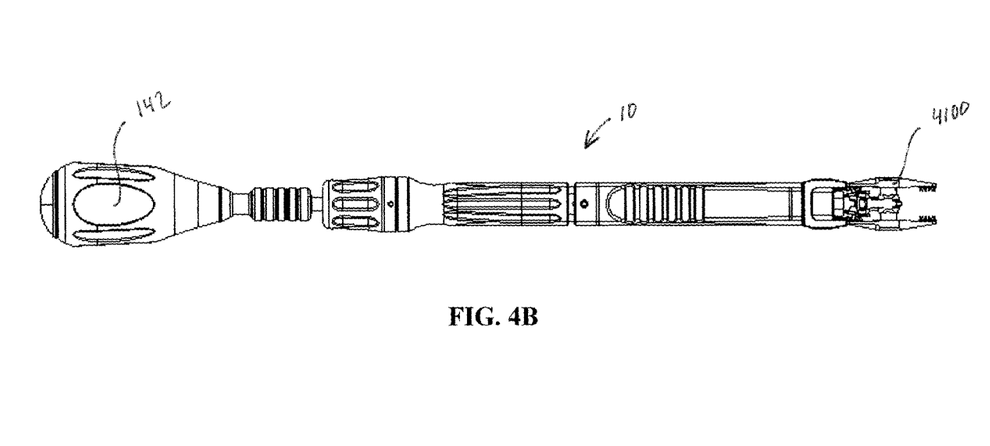

FIGS. 4A-B illustrate one embodiment of an instrument 140 used for actuating an implant, such as implant 4100. Instrument 140 includes a handle 142 and a drive shaft 144 having ears 146 at an end thereof. Drive shaft 144 is sized to extend through instrument 10, in particular through a knob cap 28 disposed inside knob insert 30. Indeed, in an embodiment, knob cap 28 is disposed inside knob insert 30, as shown in FIGS. 2C and 3C, and knob cap 28 has a diameter that is only slightly greater than a diameter of drive shaft 144. Thus, drive shaft 144 of instrument 140 is able to pass through knob cap 28 and, owing to the continuous cannulation through instrument 10 (e.g., through knob 22, knob insert 30, drive insert 36, handle 20, activation sleeve 80, spring 130, activation sleeve collar 120, spring clip 60, and sleeve 70, each of which is hollow), instrument 140 is movable relative to and within instrument 10. Once inserted inside instrument 10 and moved distally so that ears 146 are adjacent implant 4100, instrument 140 is engageable with implant 4100 to cause compression or distraction of implant 4100. In particular, ears 146 can engage female mating features 160 of actuator adjuster 4134 and, upon rotation of instrument 140 relative to and within instrument 10, actuator adjuster 4134 is rotated to cause compression or distraction of wings 4110 of implant 4100.

Instrument 10 is usable along with instrument 140—and optionally an access portal such as a cannula, retractor, or the like—to insert implant 4100 into the body of a patient in a minimally-invasive manner, as follows. In an embodiment, knob 22 may first be rotated in a counterclockwise direction to cause likewise counterclockwise rotation of knob insert 30, resulting in proximal movement of drive insert 36 (and drive rails 50 and sleeve 70 attached thereto). In this condition, arms 62 of spring clip 60 may extend from opening 74 of sleeve 70 with sleeve 70 in its first position not covering or only covering a portion of arms 62. Arms 62 of spring clip 60 are therefore able to, for example, move slightly (e.g., outwards) and engage with female mating features 170 of body 4144 of implant 4100. As arms 62 pass over female mating features 170, hooks 64 engage with female mating features 170, thereby engaging instrument 10 with implant 4110. Then, knob 22 may be rotated clockwise to cause likewise clockwise rotation of knob insert 30, resulting in distal movement of drive insert 36 (and drive rails 50 and sleeve 70 attached thereto). Knob 22 is rotated until resistance is felt and sleeve 70 is in its second position covering arms 62 of spring clip 60 and placing arms 62 in a locked state. In other words, with sleeve 70 covering arms 62, arms 62 are locked in engagement with female mating features 170 of implant 4110 and instrument 10 is securely engaged with implant 4100. In this condition, implant 4100 and swivel tip 100 are in their horizontal orientations with activation sleeve 80 biased in a distal direction by way of spring 130. Indeed, spring 130 is positioned about projection 128 of activation sleeve collar 120 and within pocket 58 of handle 20. Pins 90 are also inserted through openings 88 of activation sleeve 80, through channels 54 in handle 20, and into openings 124 of activation sleeve collar 120. As spring 130 acts on activation sleeve collar 120 (e.g., the step between main body 124 and projection 128), collar 120 and consequently activation sleeve 80 are forced in a distal direction.

To move swivel tip 100 and implant 4100 from their horizontal orientations to their vertical orientations—for insertion through an access portal in a minimally-invasive manner—the user simply pulls gripping part 82 of activation sleeve 80 to move activation sleeve 80 proximally against the force of spring 130. In particular, activation sleeve collar 120 moves proximally against spring 130, while being guided by pins 90 inserted through openings 88 of activation sleeve 80 and channels 54 of handle 20. As activation sleeve 80 moves proximally, swivel tip 100 also moves proximally creating sufficient spacing from implant 4100 for swivel tip 100 to be rotated to its vertical orientation, as shown in FIGS. 3A-C. In an embodiment, swivel tip 100 must be rotated manually against the action of torsion springs 112, although it is contemplated that an automatic mechanism may be provided to move swivel tip 100 to its vertical orientation. With swivel tip 100 in its vertical orientation, implant 4110 can be rotated to its vertical orientation so that the curved ends of wings 4110a, 4110b nest in recesses 110 of arms 104, 106 of swivel tip 100. In an embodiment, implant 4100 must be rotated manually to its vertical orientation, although it is contemplated that an automatic mechanism may be provided to move implant 4100 to its vertical orientation. At this point, activation sleeve 80 may be released so that recesses 110 of swivel tip 100 are forced distally by the action of spring 130 against wings 4110a, 4110b, thereby securing swivel tip 100 and implant 4100 in their vertical orientations. In an embodiment, activation sleeve 80 may include a set of stops 81 that form roughly an L-shape near swivel tip 100, and such stops 81 may act to help prevent rotation of swivel tip 100 and implant 4100 from their vertical orientation when activation sleeve 80 is released.

With implant 4100 and swivel tip 100 in their vertical orientations, instrument 10 with implant 4100 attached can be inserted through the minimally-invasive access portal. Since implant 4100 does not have a large footprint in its vertical orientation, it is possible to insert instrument 10 and implant 4100 through a relatively small access portal (e.g., an access portal having a diameter that is slightly larger than the footprint of implant 4100 in its vertical orientation). As implant 4100 approaches the surgical site, which in some embodiments is the spinal column of a patient, in particular the spinous processes, implant 4100 may exit the access portal and instrument 10 may be actuated to cause implant 4100 and swivel tip 100 to rotate back to their horizontal orientations. In particular, after implant 4100 exits beyond the extent of the access portal (e.g., the tips of the retractor blades or the cannula), the user may pull gripping part 82 of activation sleeve 80 proximally once more to cause swivel tip 100 to move proximally away from wings 4110 of implant 4100. With sufficient clearance between wings 4110 and swivel tip 100, torsion springs 112 may then cause swivel tip 100 to automatically assume its horizontal orientation. In other words, torsion springs 112, due to their natural bias, cause swivel tip 100 to rotate from its vertical orientation to its horizontal orientation. This causes swivel tip 100 to disengage from wings 4110 of implant 4100 and assume its horizontal orientation, while implant 4100 may remain in its vertical orientation.

Then, after release of gripping part 82, activation sleeve 80 can snap back to its normal distal position due to the force borne on activation sleeve collar 120 via spring 130. Such action causes swivel tip 100—in its horizontal orientation—to contact wings 4110 of implant 4100 and rotate implant 4100 from its vertical orientation (if it did not already rotate) to its horizontal orientation, as shown in FIGS. 2A-C. Since a surface of swivel tip 100 contacts wings 4110 of implant 4100 with force during this process (e.g., due to the action of spring 130 and the movement of swivel tip 100 distally), implant 4100 may be securely retained in its horizontal orientation. Stated differently, spring 130 may be designed to provide a sufficient amount of force against implant 4100 via contact between swivel tip 100 and wings 4110, such that implant 4100 remains securely in its horizontal orientation for implantation at the surgical site. With swivel tip 100 contacting wings 4110—both in their horizontal orientation, as shown in FIGS. 2A-C—neither swivel tip 100 nor implant 4100 can rotate to their vertical orientations. Both swivel tip 100 and implant 4100 are securely in the horizontal orientation for implantation at the surgical site.

With implant 4100 in its horizontal orientation, wings 4110 can be positioned about the patient's spinous processes, in the manner described in the '339 Publication. Then, to secure implant 4100 to the patient's spinous processes, instrument 140 is used. In a particular embodiment, the user grasps handle 142 and inserts drive shaft 144 through instrument 10, specifically through knob cap 28 and the rest of the continuous cannulation of instrument 10, so that ears 146 engage female mating features 160 of actuator adjuster 4134. Due to knob cap 28's diameter, which is only slightly greater than the diameter of drive shaft 144, instrument 140 can be inserted through instrument 10 in a controlled manner. The user rotates handle 142 with ears 146 engaged to female mating features 160, causing actuator adjuster 4134 to rotate and move actuator 4132 inwards towards wings 4110 within body 4144, resulting in wings 4110 moving towards a compressed state. Wings 4110 can then be clamped to the patient's spinous processes with sufficient force to ensure implant 4100 is stably implanted in the patient. Such clamping is described more particularly in the '339 Publication.

Instrument 140 is subsequently removed from instrument 10 once implant 4100 is secure. The user may then rotate knob 22 counterclockwise so that sleeve 70 moves in a proximal direction back to its first position. Arms 62 of spring clip 60 are then free to disengage with female mating features 170 of body 4144, for instance simply by the user pulling proximally on gripping part 44 of handle 20 and causing hooks 64 to slide off female mating features 170. In other words, in its first position sleeve 70 does not cover or only partly covers arms 62 of spring clip 60 and, by pulling proximally on handle 20, the user can cause hooks 64 to simply slide off female mating features 170 to disconnect instrument 10 from implant 4100. With the above procedure, implant 4100 is implanted on the patient's spinous processes with less trauma, decreased operating time, and decreased recovery time due to the procedure's minimally-invasive nature.

In the devices depicted in the figures, certain structures are referenced. It is understood that other equivalent structures may be used. As an example, although knob 22 is described as being connected to handle 20 via two (2) pins 90 engaged in groove 48, it is contemplated that a single pin or more than two (2) pins 90 could be used. Additionally, groove 48 may extend entirely around first projection 46 of handle 20, or it may extend only partly around first projection 46. Further, biasing members other than spring 130 can be used in instrument 10 (e.g., a flexible/compressible cylinder, etc.)

Figure 6A:
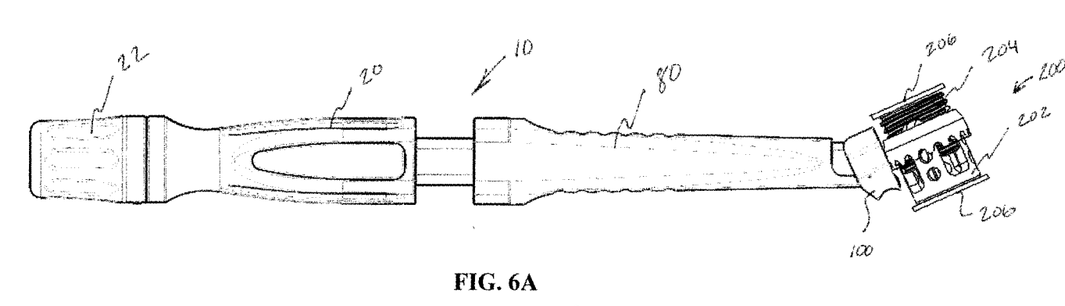
Figure 6B:
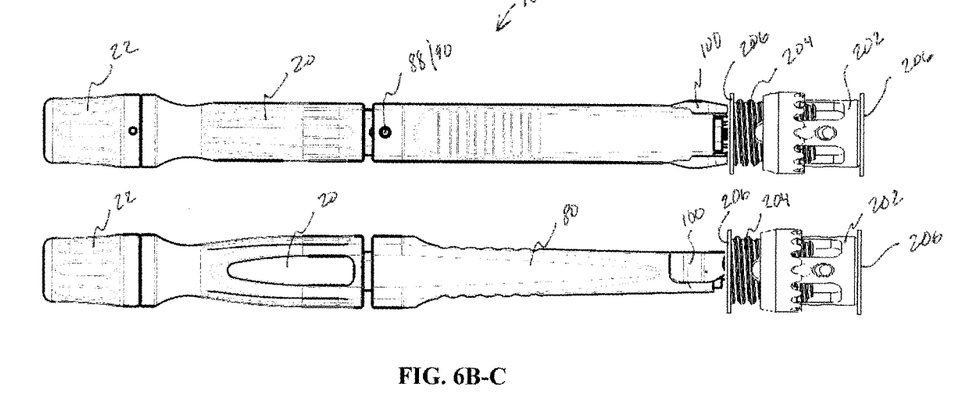

Additionally, it is contemplated that instruments 10, 140 can be used with different types of implants. As an example, FIGS. 6A-C illustrate instrument 10 in use with a corpectomy cage 200. Corpectomy cage 200 includes a first body 202 and a second body 204 that is threaded and received within first body 202. Rotation of second body 204 relative to first body 202 causes expansion or contraction of corpectomy cage 200 (e.g., to correspond to the size of a removed vertebral body of the patient). Additionally, corpectomy cage 200 includes bone-contacting surfaces 206 for contacting vertebral endplates once implanted.

As shown in FIG. 6A, corpectomy cage 200 can be placed in a horizontal orientation much like implant 4100 above. In the horizontal orientation, swivel tip 100 is also in a horizontal orientation contacting corpectomy cage 200. Further, corpectomy cage 200 and swivel tip 100 can be moved to a vertical orientation, much in the same way as detailed previously. Here, activation sleeve 80 may be retracted, and then swivel tip 100 and corpectomy cage 200 moved to their vertical orientations (e.g., manually) for insertion through an access portal. In this condition, arms 104, 106 of swivel tip 100 contact one of bone-contacting surfaces 206 of corpectomy cage 200 to secure cage 200 in its vertical orientation. As with above, after being moved through the access portal, activation sleeve 80 can be retracted, swivel tip 100 moved back to its horizontal orientation, and corpectomy cage 200 also moved to its horizontal orientation for implantation between first and second vertebrae of the patient (e.g., after an intermediate vertebrae is removed, as is common in corpectomy procedures). Additionally, instrument 140 (or another instrument, not shown) may then be inserted through instrument 10 to expand or contract corpectomy cage 200. Thus, it is to be appreciated that instruments 10, 140 are usable with a variety of implants in the manner discussed above.

Although aspects of the invention herein have been described with reference to particular embodiments, it is to be understood that these embodiments are merely illustrative of certain features of the present invention. It is therefore to be understood that numerous modifications may be made to the illustrative embodiments and that other arrangements may be devised without departing from the spirit and scope of the present invention as defined by the appended claims. For instance, the features described in connection with individual embodiments may be shared with others of the described embodiments.

It will also be appreciated that the various dependent claims and the features set forth therein can be combined in different ways than presented in the initial claims. In particular, each feature from the dependent claims may be shared with other features of other claims, to the extent technologically feasible, as if the claims were written in multiple dependent format.

The invention claimed is:

1. A method of performing surgery comprising:
engaging a first surgical instrument with an implant;
moving a pivoting member of the first surgical instrument from a first distal position to a second relatively more proximal position;
rotating the pivoting member from a first orientation in which the pivoting member occupies a first footprint in a horizontal direction to a second orientation in which the pivoting member occupies a second footprint in the horizontal direction smaller than the first footprint;
rotating the implant from a first orientation in which the implant occupies a first footprint in the horizontal direction to a second orientation in which the implant occupies a second footprint in the horizontal direction smaller than the first footprint;
subsequently biasing a surface of the pivoting member against the implant so that the pivoting member and the implant are secured in their second orientations;
inserting the instrument with the implant attached in its second orientation through an access portal extending through skin and tissue of a patient;
after the implant passes through the access portal, rotating the pivoting member from its second orientation back to its first orientation;
engaging the pivoting member with the implant so that the implant is rotated from its second orientation back to its first orientation; and
engaging the implant to anatomy in the patient.

2. A method of performing surgery as claimed in claim 1, further comprising (i) inserting a second surgical instrument through the first surgical instrument, (ii) engaging the second surgical instrument with the implant, and (iii) moving the second surgical instrument while engaged to the implant so that the implant either expands or contracts.

3. A method of performing surgery as claimed in claim 2, wherein the implant is an interspinous spacer, and the method further comprises positioning wings of the interspinous spacer about first and second spinous processes of the patient and compressing the wings against the spinous processes via step (i) of claim 2.

4. A method of performing surgery as claimed in claim 1, further comprising moving a locking mechanism of the first instrument from an unlocked state to a locked state so as to lock a connection mechanism to the implant and securely engage the implant with the first instrument.

5. A method of performing surgery as claimed in claim 4, further comprising rotating a knob of the first instrument so as to move the locking mechanism between its unlocked and locked states.

6. A method of performing surgery as claimed in claim 1, further comprising moving a spring-loaded activation sleeve of the first surgical instrument from a first distal position to a second relatively more proximal position, the activation sleeve being biased towards the first position via the spring.

* * * * *